(12) United States Patent
Okamoto et al.

(10) Patent No.: US 10,863,908 B2
(45) Date of Patent: Dec. 15, 2020

(54) SENSOR INCLUDING A STRUCTURE BODY HAVING A DEFORMING PORTION AND A FIRST SENSING ELEMENT PROVIDED AT THE DEFROMING PORTION AND MICROPHONE, BLOOD PRESSURE SENSOR, AND TOUCH PANEL INCLUDING SAME

(71) Applicant: KABUSHIKI KAISHA TOSHIBA, Tokyo (JP)

(72) Inventors: Kazuaki Okamoto, Kanagawa (JP); Yoshihiko Fuji, Kanagawa (JP); Yoshihiro Higashi, Ishikawa (JP); Shotaro Baba, Kanagawa (JP); Michiko Hara, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 29 days.

(21) Appl. No.: 16/293,689

(22) Filed: Mar. 6, 2019

(65) Prior Publication Data
US 2020/0069199 A1    Mar. 5, 2020

(30) Foreign Application Priority Data

Aug. 29, 2018 (JP) .................................. 2018-160335

(51) Int. Cl.
*G06F 3/041* (2006.01)
*H04R 15/00* (2006.01)
(Continued)

(52) U.S. Cl.
CPC ........ *A61B 5/02141* (2013.01); *B81B 3/0078* (2013.01); *G01L 1/125* (2013.01);
(Continued)

(58) Field of Classification Search
CPC ....... G01L 9/0044; G01L 9/16; G01L 9/0048; G01L 1/12; G01L 1/125; G01L 9/0051;
(Continued)

(56) References Cited

U.S. PATENT DOCUMENTS 6,690,163 B1    2/2004  Hoshiya et al.
8,139,405 B2 *  3/2012  Yoshikawa ........... H01L 27/228
                                                          365/158
(Continued)

FOREIGN PATENT DOCUMENTS

JP    2000-215414 A    8/2000
JP    2013-196243 A    9/2013
(Continued)

*Primary Examiner* — Brandi N Hopkins
(74) *Attorney, Agent, or Firm* — Finnegan, Henderson, Farabow, Garrett & Dunner, L.L.P.

(57) ABSTRACT

A sensor includes a structure body including a deforming portion, and a first sensing element provided at the deforming portion. The first sensing element includes first to fourth magnetic layers and a first intermediate layer. The first magnetic layer is provided between the second and third magnetic layers. The fourth magnetic layer is provided between the first and third magnetic layers. The first intermediate layer is provided between the second and first magnetic layers. The third magnetic layer includes at least one of a first material or a second material. The first material includes at least one selected from the group consisting of Ir—Mn, Pt—Mn, Pd—Pt—Mn, and Ru—Rh—Mn. The second material includes at least one of CoPt, $(Co_xPt_{100-x})_{100-y}Cr_y$, or FePt. A crystallinity of at least a portion of the fourth magnetic layer is higher than a crystallinity of the first magnetic layer.

20 Claims, 7 Drawing Sheets

(51) Int. Cl.
*A61B 5/021* (2006.01)
*G01L 1/12* (2006.01)
*B81B 3/00* (2006.01)
*H04R 19/04* (2006.01)

(52) U.S. Cl.
CPC .......... G06F 3/0414 (2013.01); H04R 19/04 (2013.01); *B81B 2201/0257* (2013.01)

(58) Field of Classification Search
CPC ...... H04R 15/00; H04R 2410/00; H04R 1/00; H01L 41/125
See application file for complete search history.

(56) References Cited

U.S. PATENT DOCUMENTS

| | | | |
|---|---|---|---|
| 2014/0137658 A1* | 5/2014 | Higashi | H04R 7/10 73/779 |
| 2014/0137668 A1* | 5/2014 | Fukuzawa | A61B 5/021 73/862.69 |
| 2015/0082901 A1 | 3/2015 | Fuji et al. | |
| 2016/0009545 A1 | 1/2016 | Fuji et al. | |
| 2019/0041285 A1* | 2/2019 | Fuji | H04R 1/46 |

FOREIGN PATENT DOCUMENTS

| | | |
|---|---|---|
| JP | 2015-61070 A | 3/2015 |
| JP | 2016-15412 A | 1/2016 |

* cited by examiner

SENSOR INCLUDING A STRUCTURE BODY HAVING A DEFORMING PORTION AND A FIRST SENSING ELEMENT PROVIDED AT THE DEFROMING PORTION AND MICROPHONE, BLOOD PRESSURE SENSOR, AND TOUCH PANEL INCLUDING SAME

CROSS-REFERENCE TO RELATED APPLICATIONS

This application is based upon and claims the benefit of priority from Japanese Patent Application No. 2018-160335, filed on Aug. 29, 2018; the entire contents of which are incorporated herein by reference

FIELD

Embodiments described herein relate generally to a sensor, a microphone, a blood pressure sensor, and a touch panel.

BACKGROUND

A sensor that uses a magnetic layer has been proposed. For example, the sensor is applied to a microphone, a blood pressure sensor, a touch panel, etc. High sensitivity of the sensor is desirable.

DETAILED DESCRIPTION

Figure 1A:
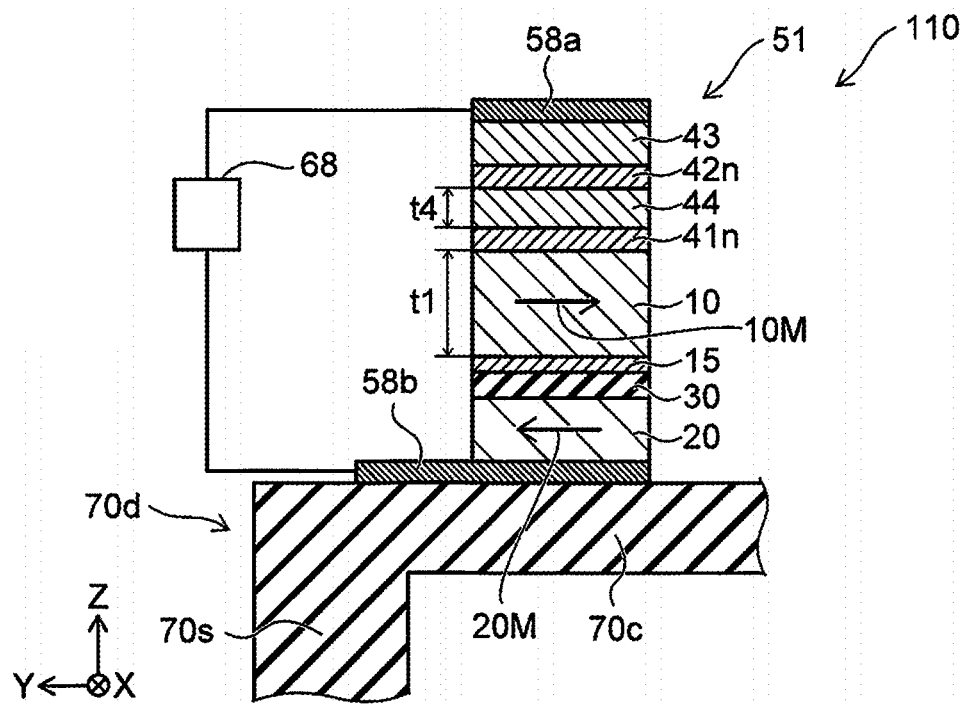
FIG. 1A and FIG. 1B are schematic views illustrating a sensor according to a first embodiment.

According to one embodiment, a sensor includes a structure body including a deforming portion, and a first sensing element provided at the deforming portion. The deforming portion is deformable. The first sensing element includes first to fourth magnetic layers and a first intermediate layer. The first magnetic layer is provided between the second magnetic layer and the third magnetic layer. The fourth magnetic layer is provided between the first magnetic layer and the third magnetic layer. The first intermediate layer is provided between the second magnetic layer and the first magnetic layer. The third magnetic layer includes at least one of a first material or a second material. The first material includes at least one selected from the group consisting of Ir—Mn, Pt—Mn, Pd—Pt—Mn, and Ru—Rh—Mn. The second material includes at least one of CoPt (a ratio of Co being not less than 50 at. % and not more than 85 at. %), $(Co_xPt_{100-x})_{100-y}Cr_y$ (x being not less than 50 at. % and not more than 85 at. %, and y being not less than 0 at. % and not more than 40 at. %), or FePt (a ratio of Pt being not less than 40 at. % and not more than 60 at. %). A crystallinity of at least a portion of the fourth magnetic layer is higher than a crystallinity of the first magnetic layer.

Various embodiments are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously or illustrated in an antecedent drawing are marked with like reference numerals, and a detailed description is omitted as appropriate.

First Embodiment

Figure 1B:
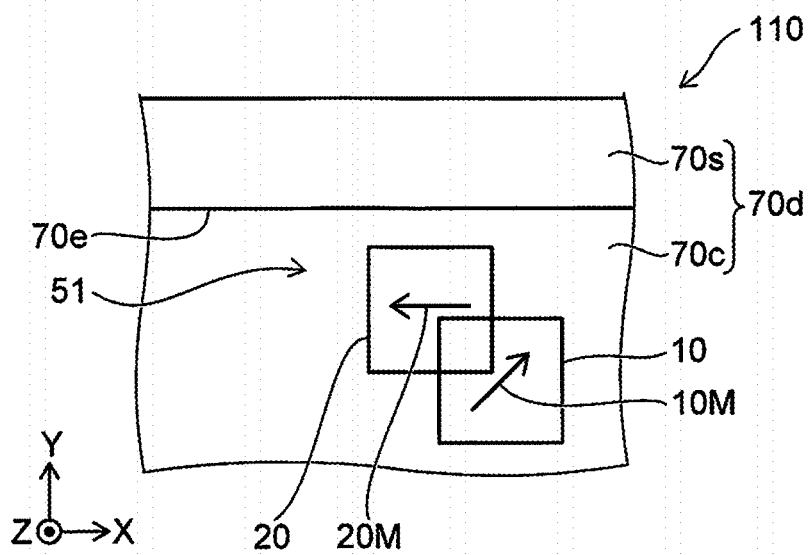

FIG. 1A and FIG. 1B are schematic views illustrating a sensor according to a first embodiment.

FIG. 1A is a cross-sectional view. FIG. 1B is a plan view. For easier viewing of the drawing in FIG. 1B, some of the components are not illustrated; and the positions of the magnetic layers are illustrated as being shifted.

As shown in FIG. 1A, the sensor 110 according to the embodiment includes a structure body 70d and a first sensing element 51.

The structure body 70d includes a deforming portion 70c. The deforming portion 70c is deformable. For example, the deforming portion 70c is supported by a supporter 70s. For example, the deforming portion 70c deforms according to a force (e.g., sound, etc.) applied to the deforming portion 70c. The deforming portion 70c may be a cantilever beam or may be a fixed beam.

The first sensing element 51 is provided at the deforming portion 70c. The first sensing element 51 is provided at a portion of the deforming portion 70c. The portion is, for example, a portion of the deforming portion 70c proximal to the supporter 70s.

The first sensing element 51 includes a first magnetic layer 10, a second magnetic layer 20, a third magnetic layer 43, a fourth magnetic layer 44, and a first intermediate layer 30.

The first magnetic layer 10 is provided between the second magnetic layer 20 and the third magnetic layer 43. The fourth magnetic layer 44 is provided between the first magnetic layer 10 and the third magnetic layer 43. The first intermediate layer 30 is provided between the second magnetic layer 20 and the first magnetic layer 10.

A first electrode 58a and a second electrode 58b are further provided in the example. The multiple magnetic layers and the first intermediate layer 30 recited above are provided between these electrodes.

The first magnetic layer 10 and the second magnetic layer 20 are, for example, ferromagnetic layers.

The direction from the second magnetic layer 20 toward the first magnetic layer 10 is taken as a first direction. The first direction is taken as a Z-axis direction. One direction perpendicular to the Z-axis direction is taken as an X-axis direction. A direction perpendicular to the Z-axis direction and the X-axis direction is taken as a Y-axis direction.

For example, the first direction corresponds to the stacking direction of the multiple magnetic layers recited above. In the example, the direction from the second electrode 58b toward the first electrode 58a is aligned with the first direction. The multiple magnetic layers recited above are arranged along the first direction between the two electrodes recited above.

For example, the orientation of a first magnetization of the first magnetic layer 10 changes more easily than the orientation of a second magnetization of the second magnetic layer 20. The first magnetic layer 10 is, for example, a free magnetic layer. The second magnetic layer 20 is, for example, a reference layer (e.g., a fixed magnetic layer).

For example, the deforming portion 70c deforms. The deformation includes, for example, a displacement along the Z-axis direction. The deformation may include elongating and contracting of at least a portion of the deforming portion 70c in a plane aligned with the X-Y plane.

The electrical resistance of the first sensing element 51 changes according to the deformation of the deforming portion 70c. For example, the orientation of the first magnetization 10M of the first magnetic layer 10 changes according to the deformation of the deforming portion 70c. The angle between the first magnetization 10M and the second magnetization 20M changes according to the deformation. For example, it is considered that the change of the angle is based on an inverse magnetostrictive effect. The electrical resistance changes due to the change of the angle. For example, it is considered that the change of the electrical resistance is based on a magnetoresistance effect.

In the embodiment, the third magnetic layer 43 includes at least one of a first material or a second material recited below. The first material includes at least one selected from the group consisting of Ir—Mn, Pt—Mn, Pd—Pt—Mn, and Ru—Rh—Mn. The second material includes at least one of CoPt (the ratio of Co being not less than 50 at. % and not more than 85 at. %), $(Co_xPt_{100-x})_{100-y}Cr_y$ (x being not less than 50 at. % and not more than 85 at. %, and y being not less than 0 at. % and not more than 40 at. %), or FePt (the ratio of Pt being not less than 40 at. % and not more than 60 at. %). For example, the third magnetic layer 43 functions as a bias applying layer.

The third magnetic layer 43 is, for example, an antiferromagnetic layer.

For example, the magnetization of the fourth magnetic layer 44 is controlled by a magnetic bias generated by exchange coupling with the third magnetic layer 43. For example, ferromagnetic exchange coupling is generated between the third magnetic layer 43 and the fourth magnetic layer 44. For example, antiferromagnetic exchange coupling is generated between the third magnetic layer 43 and the fourth magnetic layer 44. It is considered that the magnetization of the first magnetization 10M of the first magnetic layer 10 is controlled by the magnetization of the fourth magnetic layer 44. Thereby, as described below, the sensitivity of the sensor 110 improves.

In the example, the first sensing element 51 further includes an intermediate magnetic layer 15, a first nonmagnetic layer 41n, and a second nonmagnetic layer 42n. The intermediate magnetic layer 15 is provided between the first magnetic layer 10 and the first intermediate layer 30. Examples of the intermediate magnetic layer are described below. The intermediate magnetic layer may be omitted. The first nonmagnetic layer 41n is provided between the first magnetic layer 10 and the fourth magnetic layer 44. The second nonmagnetic layer 42n is provided between the fourth magnetic layer 44 and the third magnetic layer 43. Examples of these magnetic layers are described below. These nonmagnetic layers may be omitted.

The thickness of the first magnetic layer 10 is taken as a first thickness t1. The thickness of the fourth magnetic layer 44 is taken as a fourth thickness t4. These thicknesses are lengths along the Z-axis direction. As described below, it is favorable for the fourth thickness t4 to be thinner than the first thickness t1.

Examples of the orientations of the magnetizations in the first sensing element 51 will now be described.

FIG. 1B schematically shows the magnetizations in the first sensing element 51. As shown in FIG. 1B, the deforming portion 70c includes a connection portion 70e connected to the supporter 70s. The connection portion 70e is aligned with a first connection direction. In the example, the first connection direction is the X-axis direction.

For example, the first magnetization 10M of the first magnetic layer 10 is tilted with respect to the first connection direction (the X-axis direction) when an external force is not applied to the deforming portion 70c (in the initial state).

When an external force is applied to the deforming portion 70c, stress (or strain) is applied to the deforming portion 70c along a direction (e.g., the Y-axis direction) crossing the first connection direction (the X-axis direction). Stress (or strain) is applied to the first magnetic layer 10 along the direction (e.g., the Y-axis direction) crossing the first connection direction (the X-axis direction).

Because the first magnetization 10M of the first magnetic layer 10 is tilted with respect to the first connection direction (the X-axis direction) in the initial state, for example, the orientation of the first magnetization 10M changes easily according to the deformation of the deforming portion 70c. For example, the resistance change of the first sensing element 51 corresponding to the change of the orientation of the first magnetization 10M is large. Even when the deformation of the deforming portion 70c is small, a change of the electrical resistance is obtained stably. A sensor can be provided in which the sensitivity can be increased. For example, the changeable region of the relative angle between the first magnetization 10M and the second magnetization 20M when the external force is applied to the deforming portion 70c can be widened. For example, the detection range is wider for the orientation and the magnitude of the force applied to the deforming portion 70c. For example, a sensor that has a wide dynamic range can be provided.

In one example, the absolute value of the angle between the first magnetization 10M and the first connection direction (the X-axis direction) is not less than 10 degrees and not more than 80 degrees. The absolute value of the angle may be not less than 20 degrees and not more than 70 degrees. The absolute value of the angle may be not less than 30 degrees and not more than 60 degrees. By such an angle, the change ratio of the electrical resistance with respect to the deformation of the deforming portion 70c can be stable and high.

In the example, the second magnetization 20M of the second magnetic layer 20 is aligned with the first connection direction (the X-axis direction). In another example, the second magnetization 20M may be substantially perpendicular to the first connection direction (the X-axis direction). For example, the first magnetization 10M of the first magnetic layer 10 is tilted with respect to the second magnetization 20M of the second magnetic layer 20. The absolute value of the angle between the first magnetization 10M and the second magnetization 20M is not less than 10 degrees and not more than 80 degrees. The absolute value of the angle may be not less than 20 degrees and not more than 70 degrees. The absolute value of the angle may be not less than 30 degrees and not more than 60 degrees. By such an angle, the change ratio of the electrical resistance with respect to the deformation of the deforming portion 70c can be stable and high.

In the embodiment, for example, the magnetization of the fourth magnetic layer 44 is controlled by the magnetic bias from the third magnetic layer 43. For example, the magnetization of the fourth magnetic layer 44 is tilted with respect to the first connection direction (the X-axis direction). It is considered that the magnetization of the first magnetization 10M of the first magnetic layer 10 is controlled thereby.

It was found that a stable magnetic bias is obtained by setting the crystallinity of at least a portion of the fourth magnetic layer 44 to be higher than the crystallinity of the first magnetic layer 10.

For example, at least a portion of the first magnetic layer 10 is amorphous. On the other hand, at least a portion of the fourth magnetic layer 44 includes a crystal. For example, at least a portion of the fourth magnetic layer 44 includes a crystalline portion.

For example, by setting the crystallinity of the first magnetic layer 10 to be low (e.g., amorphous), a low coercivity is obtained in the first magnetic layer 10. Thereby, the ease of the change of the orientation of the first magnetization 10M with respect to the strain (the deformation) can be obtained.

On the other hand, a reference example may be considered in which only the first magnetic layer 10 that has low crystallinity (e.g., being amorphous) is provided; and the fourth magnetic layer 44 is not provided. It was found that in such a case, a sufficient magnetic bias is not obtained from the third magnetic layer 43. It is considered that this is because when the third magnetic layer 43 is provided on the first magnetic layer 10 having the low crystallinity, the crystal quality of the third magnetic layer 43 degrades; and the exchange coupling between the third magnetic layer 43 and the first magnetic layer is not generated or is small.

In the embodiment, the fourth magnetic layer 44 that has high crystallinity is provided. Thereby, good crystal quality is obtained in the third magnetic layer 43 provided on the fourth magnetic layer 44. Thereby, the magnetic bias from the third magnetic layer 43 can be sufficiently large. For example, the magnetization of the fourth magnetic layer 44 can be controlled to the desired direction by the magnetic bias from the third magnetic layer 43. The first magnetization 10M of the first magnetic layer 10 can be controlled to the desired orientation by the controlled magnetization of the fourth magnetic layer 44. For example, as illustrated in FIG. 1B, the orientation of the first magnetization 10M crosses the X-axis direction. The orientation of the first magnetization 10M may be tilted with respect to the X-axis direction.

For example, the magnetization of the fourth magnetic layer 44 can be controlled by performing heat treatment at a high temperature in a magnetic field; and the first magnetization 10M of the first magnetic layer 10 can be controlled to the desired orientation.

In the embodiment, the first magnetic layer 10 has a high magnetostriction coefficient and a low coercivity. The fourth magnetic layer 44 has a high magnetostriction coefficient and high coercivity. Thereby, a large change of the electrical resistance is easier to obtain according to the deformation of the deforming portion 70c. On the other hand, for example, in the case of a reference example that detects a magnetic field, the magnetostriction coefficient may be low.

Figure 2:
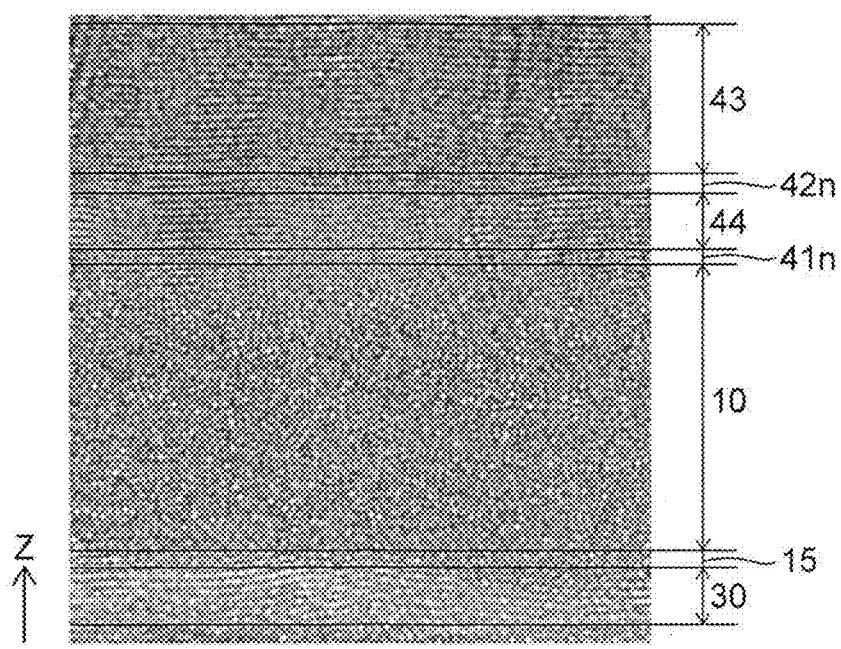
FIG. 2 is a transmission electron microscope image of a portion of the sensor.

FIG. 2 is a transmission electron microscope image of a portion of the sensor.

FIG. 2 is a transmission electron microscope (TEM) image of a sample corresponding to the sensor 110. The sample has the configuration illustrated in FIG. 1A.

In the sample, the deforming portion 70c is a $SiO_2$ film. The $SiO_2$ film is provided on a silicon substrate. The second electrode 58b is a stacked film of Ta/Cu/Ta. A Ta film (having a thickness of 2 nm), a Ru film (having a thickness of 2 nm), and a $Pt_{41}Mn_{59}$ film (having a thickness of 20 nm) are provided in this order on the second electrode 58b. Then, a $Co_{90}Fe_{10}$ film (having a thickness of 2.5 nm), a Ru film (having a thickness of 0.85 nm), and a $Co_{40}Fe_{40}B_{20}$ film (having a thickness of 2.5 nm) are provided in this order. For example, the stacked film of the $Co_{90}Fe_{10}$ film (having a thickness of 2.5 nm), the Ru film (having a thickness of 0.85 nm), and the $Co_{40}Fe_{40}B_{20}$ film is considered to be the second magnetic layer 20. For example, the $Co_{40}Fe_{40}B_{20}$ film may be considered to be the second magnetic layer 20.

The first intermediate layer 30 is a MgO film (having a thickness of 1.8 nm). The intermediate magnetic layer 15 is a $Co_{40}Fe_{40}B_{20}$ film (having a thickness of 0.5 nm). The first magnetic layer 10 is an $Fe_{80}B_{20}$ film (having a thickness of 8 nm). The first nonmagnetic layer 41n is a Cu film (having a thickness of 0.4 nm). The fourth magnetic layer 44 is an $Fe_{50}Co_{50}$ film (having a thickness of 1.6 nm). The second nonmagnetic layer 42n is a Cu film (having a thickness of 0.65 nm). The third magnetic layer 43 is $Ir_{22}Mn_{78}$ (having a thickness of 4 nm).

In the sample, a Ru film (having a thickness of 2 nm), a Ta film (having a thickness of 2 nm), and a Ru film (having a thickness of 21 nm) are provided in this order on the third magnetic layer 43. The first electrode 58a is provided on the Ru film (having the thickness of 21 nm). The first electrode 58a is a stacked film of a Ta film/Cu film/Ta film.

It can be seen from FIG. 2 that the crystallinity of the first magnetic layer 10 is low. The first magnetic layer 10 is substantially amorphous. Conversely, fringes that correspond to a crystal are observed in the fourth magnetic layer 44. The distinctness of the fringes (the crystallinity) in the fourth magnetic layer 44 is substantially similar to the distinctness of the fringes (the crystallinity) in the first intermediate layer 30.

It can be seen from FIG. 2 that fringes corresponding to a crystal are observed in the third magnetic layer 43 as well. The crystallinity of the third magnetic layer 43 is higher than the crystallinity of the first magnetic layer 10.

Thus, the crystallinity of at least a portion of the fourth magnetic layer 44 is higher than the crystallinity of the first magnetic layer 10. Thereby, good crystal quality is obtained in the third magnetic layer 43. Thereby, the magnetic bias from the third magnetic layer 43 can be sufficiently large. The magnetization of the fourth magnetic layer 44 can be controlled stably to the desired direction. The first magnetization 10M of the first magnetic layer 10 is controlled stably to the desired orientation by the magnetic bias from the fourth magnetic layer 44. For example, the first magnetic layer 10 and the third magnetic layer 43 are ferromagnetically coupled.

The set of the first magnetic layer 10 and the fourth magnetic layer 44 functions as a strain sensing layer.

In the embodiment, because the crystallinity of the fourth magnetic layer 44 is high, if the thickness of the fourth magnetic layer 44 becomes excessively thick, there are cases where the coercivity is excessively large for the entire strain sensing layer (the first magnetic layer 10 and the fourth magnetic layer 44). If the coercivity is excessively large, the sensitivity of the sensor decreases.

Therefore, it is favorable for the thickness of the fourth magnetic layer 44 (the fourth thickness t4 referring to FIG. 1A) to be thin. For example, it is sufficient for the fourth thickness t4 to be thick enough for good crystallinity to be obtained in the fourth magnetic layer 44.

An example of measurement results of changes of the magnetic characteristics when modifying the fourth thickness t4 will now be described. The following samples are made for the measurement. A stacked body of a Si substrate/Cu (1 nm)/MgO layer (1.8 nm)/$Co_{40}Fe_{40}B_{20}$ (0.5 nm)/$Fe_{80}B_{20}$ (8 nm)/$Co_{50}Fe_{50}$/$Ir_{22}Mn_{78}$ (12 nm)/Ru (2 nm)/Ta (3 nm) is provided in each sample. In the description recited above, the lengths inside the parentheses each are the thicknesses of the layers. The Cu layer is a foundation layer. The MgO layer corresponds to the first intermediate layer 30. The $Co_{40}Fe_{40}B_{20}$ layer corresponds to the intermediate magnetic layer 15. The $Fe_{80}B_{20}$ layer corresponds to the first magnetic layer 10. The $CO_{50}Fe_{50}$ layer corresponds to the fourth magnetic layer 44. The $Ir_{22}Mn_{78}$ corresponds to the third magnetic layer 43. The Ru (2 nm) and the Ta (3 nm) correspond to the first electrode 58a. The second magnetic layer 20 is not provided in the samples. The thickness (the first thickness t1) of the $Fe_{80}B_{20}$ layer (the first magnetic layer 10) is 8 nm and is constant. In the experiment, the thickness (the fourth thickness t4) of the $Co_{50}Fe_{50}$ layer (the fourth magnetic layer 44) is modified in the range of 0.5 nm to 4 nm. The characteristics of the strain sensing layer (the set of the first magnetic layer 10 and the fourth magnetic layer 44) are evaluated using such samples.

In the evaluation, the H-M characteristic is evaluated.

Figure 3:
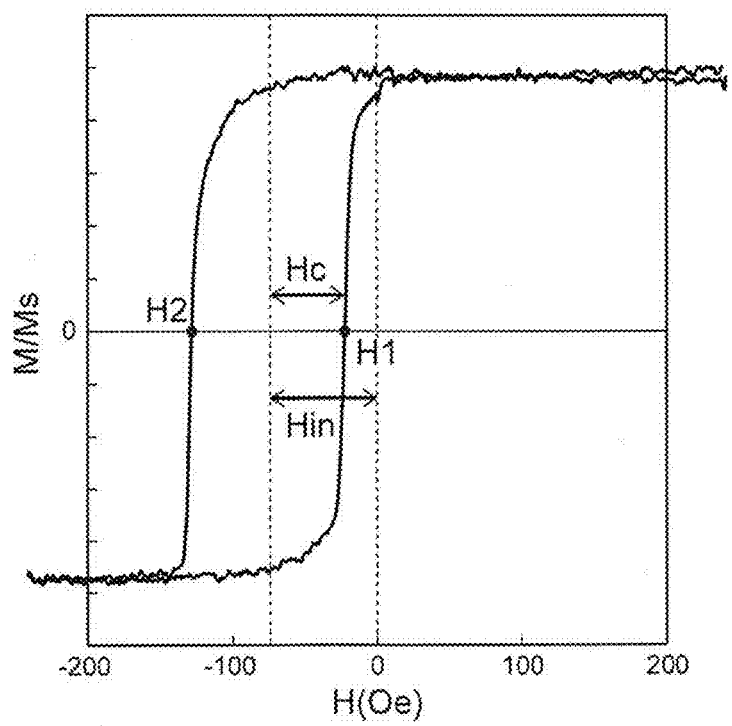
FIG. 3 is a schematic view illustrating a magnetic characteristic.
Figure 4A:
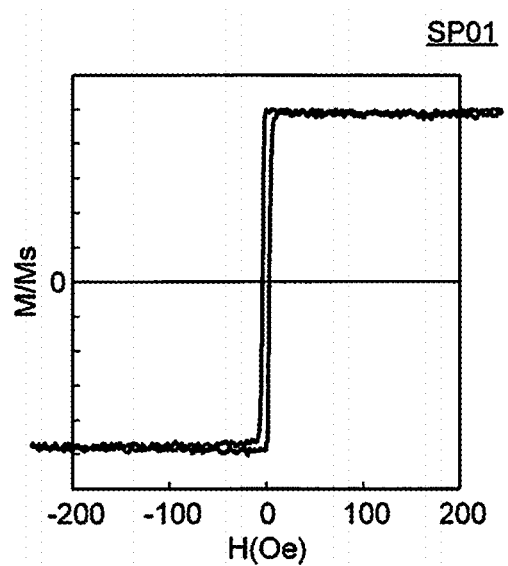
FIG. 4A to FIG. 4D are graphs illustrating magnetic characteristics.
Figure 4B:
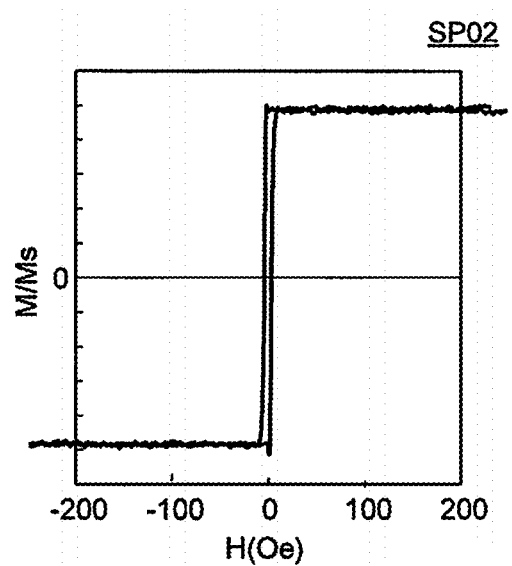
Figure 4C:
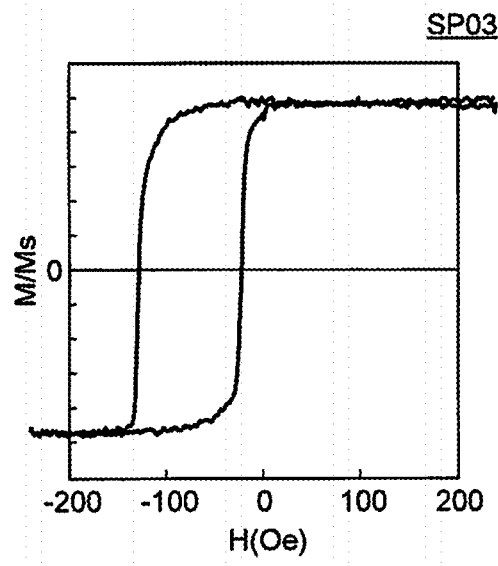
Figure 4D:
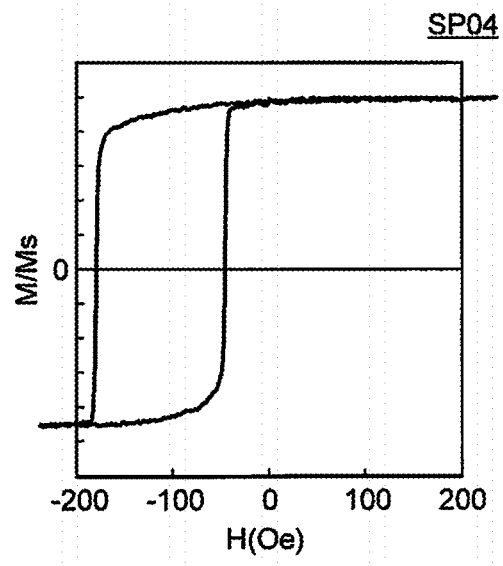

FIG. 3 is a schematic view illustrating a magnetic characteristic.

The horizontal axis of FIG. 3 is an external magnetic field H (Oe). The vertical axis is a parameter M/Ms corresponding to the magnitude of the magnetization of the strain sensing layer (the set of the first magnetic layer 10 and the fourth magnetic layer 44). The external magnetic field H (Oe) is aligned with the direction of the magnetic bias.

As shown in FIG. 3, hysteresis occurs in the H-M characteristic. A first value H1 and a second value H2 occur. ½ of the difference between the first value H1 and the second value H2 corresponds to a coercivity Hc. The difference between the external magnetic field H of 0 and the midpoint between the external magnetic field corresponding to the first value H1 and the external magnetic field corresponding to the second value H2 is taken as a value Hin. The value Hin corresponds to the magnitude of the magnetic bias. For example, the value Hin is 0 for a sample in which the fourth magnetic layer 44 is not provided.

The evaluation results of the first to fourth samples will now be described.

FIG. 4A to FIG. 4D are graphs illustrating magnetic characteristics.

FIG. 4A to FIG. 4D correspond respectively to the first to fourth samples SP01 to SP04. The fourth thickness t4 is 0.5 nm, 1.0 nm, 1.6 nm, and 4.0 nm respectively for the first to fourth samples SP01 to SP04.

In the first sample SP01, the coercivity Hc is 3 Oe; and the value Hin is 0 Oe.

In the second sample SP02, the coercivity Hc is 3 Oe; and the value Hin is 0 Oe. In the third sample SP03, the coercivity Hc is 55 Oe; and the value Hin is 75 Oe.

In the fourth sample SP04, the coercivity Hc is 70 Oe; and the value Hin is 110 Oe.

Figure 5A:
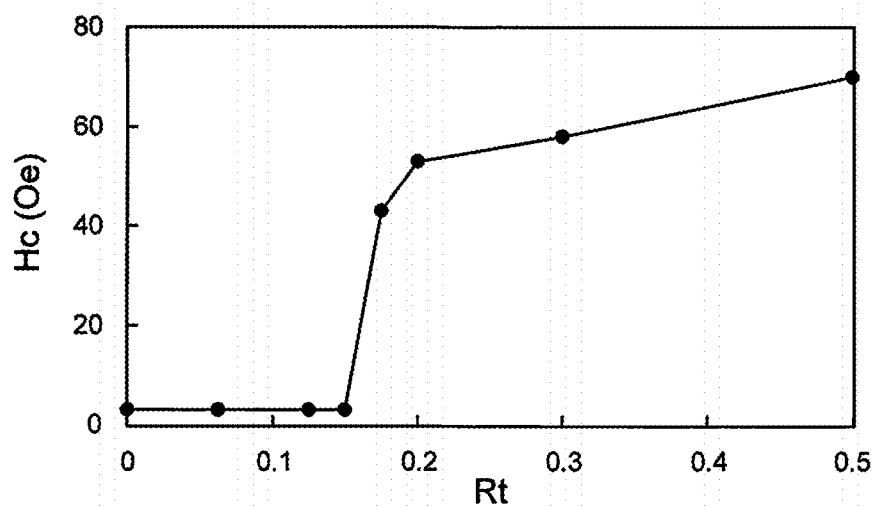
FIG. 5A and FIG. 5B are graphs illustrating magnetic characteristics.
Figure 5B:
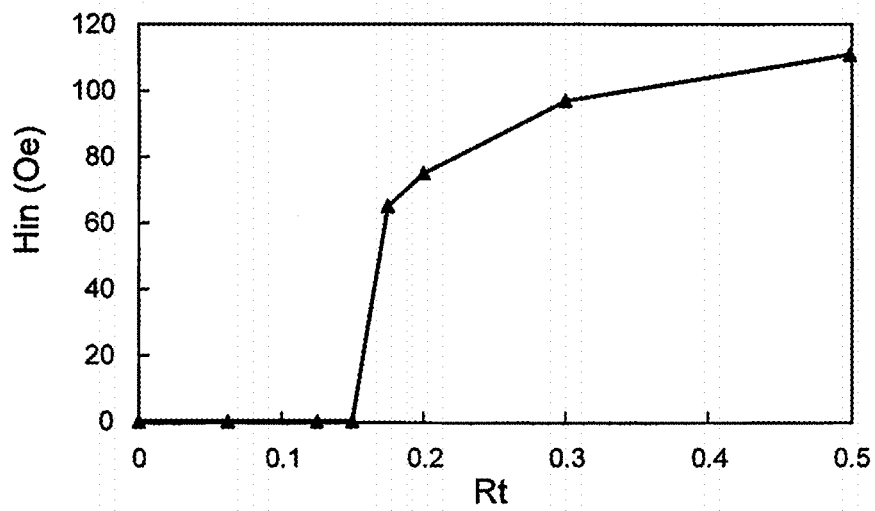

FIG. 5A and FIG. 5B are graphs illustrating magnetic characteristics.

In these figures, the horizontal axis is a thickness ratio Rt. The thickness ratio Rt is the ratio (t4/t1) of the fourth thickness t4 to the first thickness t1. The vertical axis of FIG. 5A is the coercivity Hc (Oe). The vertical axis of FIG. 5B is the value Hin (Oe). These figures show the results of the first to fourth samples SP01 to SP04 recited above and the results of other samples. The thickness ratio Rt is 0.065, 0.125, 0.2, and 0.5 respectively for the first to fourth samples SP01 to SP04. In the first to fourth samples SP01 to SP04 and the other samples, the thickness (the first thickness t1) of the $Fe_{80}B_{20}$ layer (the first magnetic layer 10) is 8 nm and is constant.

As shown in FIG. 5A and FIG. 5B, the coercivity Hc and the magnetic bias value Hin increase abruptly when the thickness ratio Rt exceeds 0.15. The coercivity Hc and the magnetic bias value Hin are distinctly large when the thickness ratio Rt is 0.175. In the example, the fourth thickness t4 of the fourth magnetic layer 44 is 1.2 nm when the thickness ratio Rt is 0.15. The fourth thickness t4 of the fourth magnetic layer 44 is 1.4 nm when the thickness ratio Rt is 0.175. It is considered that the crystallinity of the fourth magnetic layer 44 is insufficient when the fourth thickness t4 of the fourth magnetic layer 44 is 1.2 nm or less. It is considered that the crystallinity of the fourth magnetic layer 44 increases abruptly when the fourth thickness t4 of the fourth magnetic layer 44 becomes a threshold (in the example, 1.4 nm) or more. Therefore, it is considered that the coercivity Hc and the magnetic bias Hin increase abruptly. In the experimental example, the threshold of the fourth thickness t4 is 1.4 nm.

For example, it is favorable for the fourth thickness t4 of the fourth magnetic layer 44 to be 1.4 nm or more. A sufficient bias value Hin is obtained when the fourth thickness t4 is 1.4 nm or more. According to the manufacturing conditions of the fourth magnetic layer 44, there are cases where the appropriate crystallinity is obtained in the fourth magnetic layer 44 even when the fourth thickness t4 is 1.2 nm or more. For example, there are cases where a sufficient bias Hin is obtained when the fourth thickness t4 is 1.2 nm or more. In the embodiment, it is favorable for the fourth thickness t4 of the fourth magnetic layer 44 to be 1.2 nm or more.

For example, it is considered that the fourth thickness t4 (e.g., the threshold of the thickness) where the coercivity Hc and the magnetic bias value Hin start to increase abruptly is about 1.4 nm. It is considered that the threshold of the thickness is substantially not affected by the distance between the first magnetic layer 10 and the fourth magnetic layer 44.

In the case where the fourth thickness t4 of the fourth magnetic layer 44 is the threshold or more (in the example, in the case where the thickness ratio Rt is 0.175 or more), the coercivity Hc and the value Hin increase gradually as the thickness ratio Rt increases.

The experimental results recited above are results when the $Fe_{80}B_{20}$ (8 nm) layer (the first magnetic layer 10) and the $Co_{50}Fe_{50}$ layer (the fourth magnetic layer 44) contact each other, and are the results when the distance between these layers is 0 nm.

The magnitude of the value Hin after the magnetic bias value Hin has increased abruptly is called the "value Hin after the change." It is considered that the "value Hin after the change" is dependent on the distance between the first magnetic layer 10 and the fourth magnetic layer 44. For example, the "value Hin after the change" when the distance between the first magnetic layer 10 and the fourth magnetic layer 44 is short is larger than the "value Hin after the change" when the distance is long.

On the other hand, it is considered that the coercivity Hc of the strain sensing layer (the set of the first magnetic layer 10 and the fourth magnetic layer 44) is substantially independent of the distance between the first magnetic layer 10 and the fourth magnetic layer 44. For example, it is considered that the coercivity Hc is dependent on the ratio (the thickness ratio Rt) of the fourth thickness t4 of the fourth magnetic layer 44 (the crystal) to the first thickness t1 of the first magnetic layer 10 (amorphous). High sensitivity is obtained when the coercivity Hc is small.

Accordingly, it is favorable for the thickness ratio Rt to be low when the fourth thickness t4 exceeds the threshold of the thickness (the thickness where the value Hin starts to increase abruptly). Thereby, for example, a small coercivity Hc is obtained. When the thickness ratio Rt is low, a small coercivity Hc and the desired magnetic bias value Hin are obtained by adjusting the distance between the first magnetic layer 10 and the fourth magnetic layer 44.

In the example as shown in FIG. 5A and FIG. 5B (the distance between the first magnetic layer 10 and the fourth magnetic layer 44 being 0), in the case where the thickness ratio Rt is 0.175, the magnitude of the magnetic bias value Hin of the strain sensing layer is sufficiently large and is about 60 Oe; and the coercivity Hc is about 50 and is low.

On the other hand, for example, the "bias value Hin after the change" when the distance between the first magnetic layer 10 and the fourth magnetic layer 44 is long (e.g., 2 nm) is smaller than the "value Hin after the change" when the distance between the first magnetic layer 10 and the fourth magnetic layer 44 is short (e.g., 0 nm or not more than about 1 nm). Accordingly, a method in which the fourth thickness t4 of the fourth magnetic layer 44 is increased may be considered to obtain the "value Hin after the change" having the desired magnitude. However, when the fourth thickness t4 is increased, the thickness ratio Rt becomes high; as a result, the coercivity Hc becomes large.

In the embodiment, it is favorable for the distance between the first magnetic layer 10 and the fourth magnetic layer 44 to be short (e.g., 0 nm or not more than about 1 nm). Thereby, the "value Hin after the change" having the desired magnitude is obtained easily. As a result, the fourth thickness t4 of the fourth magnetic layer 44 can be thin; and the thickness ratio Rt can be low. For example, the thickness ratio Rt can be 0.25 or less. Thereby, the coercivity Hc can be maintained to be low. High sensitivity is obtained thereby.

In the embodiment, for example, it is favorable for the ratio (the thickness ratio Rt) of the fourth thickness t4 of the fourth magnetic layer 44 to the first thickness t1 of the first magnetic layer 10 to exceed 0.125. A sufficiently large magnetic bias Hin is obtained thereby.

By setting the thickness ratio Rt to be low, for example, the increase of the coercivity Hc can be suppressed. For example, it is favorable for the thickness ratio Rt to be 0.3 or less. It is more favorable for the thickness ratio Rt to be 0.25 or less. For example, the coercivity Hc can be suppressed to be about 60 Oe or less. For example, high sensitivity is obtained easily.

The fourth thickness t4 of the fourth magnetic layer 44 is, for example, 1.2 nm or more. Thereby, for example, good crystallinity of the fourth magnetic layer 44 is obtained; and a sufficiently large magnetic bias Hin can be obtained. The first thickness t1 of the first magnetic layer 10 is, for example, 5 nm or more. Thereby, the coercivity Hc of the strain sensing layer can be maintained to be low.

In one example, the first magnetic layer 10 includes Fe and B. The fourth magnetic layer 44 includes Fe, Co, and Ni.

As described above, the intermediate magnetic layer 15 may be provided (referring to FIG. 1A). For example, the intermediate magnetic layer 15 includes Fe, Co, and B. The concentration of Co included in the first magnetic layer 10 is lower than the concentration of Co included in the intermediate magnetic layer 15. Or, the first magnetic layer 10 does not include Co.

The intermediate magnetic layer 15 may include a crystalline portion. For example, the intermediate magnetic layer 15 functions as a transition region of the crystallinity between the first intermediate layer 30 (e.g., the crystal layer) and the first magnetic layer 10 (e.g., the amorphous layer).

As described above, the first nonmagnetic layer 41n may be further provided (referring to FIG. 1A). The first nonmagnetic layer 41n includes, for example, at least one selected from the group consisting of Cu, Ru, Au, Ag, Cr, Ir, and Mg. The thickness of the first nonmagnetic layer 41n is not less than 0.1 nm and not more than 2 nm. For example, the first nonmagnetic layer 41n contacts the first magnetic layer 10 and the fourth magnetic layer 44.

For example, the first nonmagnetic layer 41n controls the strength of the magnetic coupling between the first magnetic layer 10 and the fourth magnetic layer 44.

As described above, the second nonmagnetic layer 42n may be further provided (referring to FIG. 1A). The second nonmagnetic layer 42n includes, for example, at least one selected from the group consisting of Cu, Ru, Au, Ag, Cr, Ir, and Mg. The thickness of the second nonmagnetic layer 42n is not less than 0.1 nm and not more than 2 nm. For example, the second nonmagnetic layer 42n contacts the fourth magnetic layer 44 and the third magnetic layer 43.

For example, the second nonmagnetic layer 42n controls the strength of the magnetic coupling between the fourth magnetic layer 44 and the third magnetic layer 43.

For example, the magnitude of the magnetic coupling applied to the strain sensing layer can be controlled by providing, for example, the first nonmagnetic layer 41n and the second nonmagnetic layer 42n. For example, the magnitude Hin of the magnetic bias applied to the strain sensing layer can be adjusted to the desired value.

The second magnetic layer 20 may be one magnetic film. In such a case, the second magnetic layer 20 includes, for example, at least one selected from the group consisting of Co, Fe, and Ni. The second magnetic layer 20 is, for example, a $Co_xFe_{100-x}$ alloy layer (0 atomic %≤x≤100 atomic %). Or, the second magnetic layer 20 may be a $Ni_xFe_{100-x}$ alloy layer (0 atomic %≤x≤100 atomic %). A nonmagnetic element may be added to these materials. The thickness of the second magnetic layer 20 is, for example, not less than 1.5 nm and not more than 5 nm. The second magnetic layer 20 may include a magnetic film and a nonmagnetic film stacked with each other. The portion that includes the stacked magnetic film and nonmagnetic film has a magnetization. For example, the orientations of the magnetizations of the multiple magnetic films included in the second magnetic layer 20 are in a mutually-antiparallel state due to synthetic antiferromagnetic coupling.

The first intermediate layer 30 (referring to FIG. 1A) includes, for example, oxygen and at least one selected from the group consisting of Mg, Al, Ti, Zn, and Ga. The thickness of the first intermediate layer 30 is, for example, not less than 0.6 nm and not more than 5 nm.

At least one of the first electrode 58a or the second electrode 58b includes, for example, at least one selected from the group consisting of aluminum (Al), aluminum copper alloy (Al—Cu), copper (Cu), silver (Ag), tantalum (Ta), and gold (Au). At least one of the first electrode 58a or the second electrode 58b may include, for example, at least one selected from the group consisting of TaMo, Ti, and TIN.

Multiple sensing elements may be provided in the embodiment.

FIG. 6A to FIG. 6D are schematic views illustrating a sensor according to the embodiment.

Figure 6A:
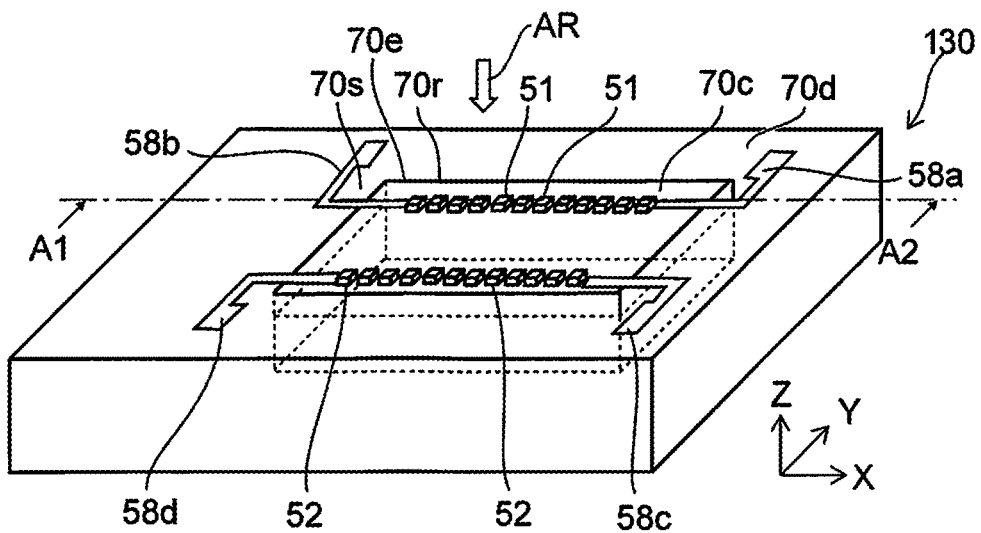
FIG. 6A to FIG. 6D are schematic views illustrating a sensor according to the embodiment.
Figures 6B, 6D:
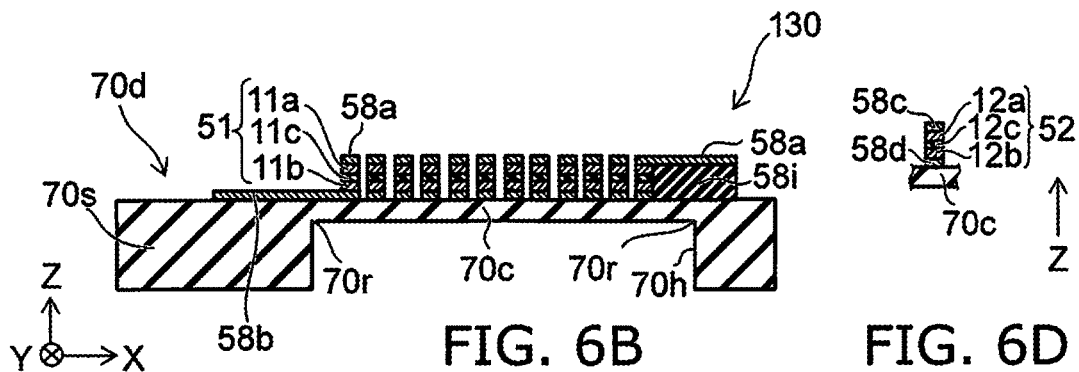
Figure 6C:
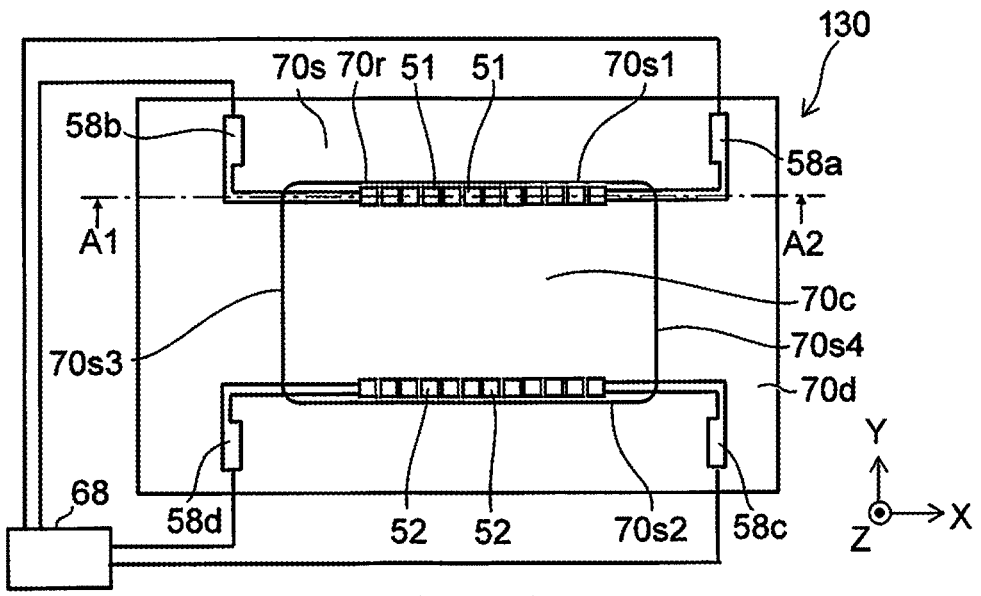

FIG. 6A is a perspective view. FIG. 6B is a line A1-A2 cross-sectional view of FIG. 6A. FIG. 6C is a plan view as viewed along arrow AR of FIG. 6A. FIG. 6D is a cross-sectional view illustrating a portion of the sensor.

As shown in FIG. 6A, the sensor 130 according to the embodiment includes the structure body 70d, the first sensing element 51, and a second sensing element 52.

The first sensing element 51 and the second sensing element 52 are fixed to the deforming portion 70c of the structure body 70d. In the example, the first sensing element 51 is fixed to a first position (a first region) of the deforming portion 70c. The second sensing element 52 is fixed to a second position (a second region) of the deforming portion 70c.

The multiple first sensing elements 51 and the multiple second sensing elements 52 are provided in the example. In the example, the multiple first sensing elements 51 are arranged along the X-axis direction. In the example, the multiple second sensing elements 52 are arranged along the X-axis direction. For example, the multiple first sensing elements 51 are connected in series to each other. For example, the multiple second sensing elements 52 are connected in series to each other. In the embodiment, the number of the first sensing elements 51 is arbitrary. The number of the second sensing elements 52 is arbitrary.

The deforming portion 70c is held by the supporter 70s. The structure body 70d has an outer edge 70r. The outer edge 70r corresponds to the connection portion 70e. The supporter 70s holds the outer edge 70r. For example, a substrate that is used to form the deforming portion 70c and the supporter 70s is provided. The substrate is, for example, a silicon substrate. A hollow 70h is provided in the substrate by removing a portion of the substrate (referring to FIG. 6B). The thin portion of the substrate is used to form the deforming portion 70c. The thick portion of the substrate is used to form the supporter 70s.

As shown in FIG. 6B, the first sensing element 51 includes a first magnetic film 11a, a first counter magnetic film 11b, and a first intermediate film 11c. The first intermediate film 11c is provided between the first magnetic film 11a and the first counter magnetic film 11b. The second sensing element 52 includes a second magnetic film 12a, a second counter magnetic film 12b, and a second intermediate film 12c. The second intermediate film 12c is provided between the second magnetic film 12a and the second counter magnetic film 12b.

For example, the first magnetic film 11a and the second magnetic film 12a correspond to the first magnetic layer 10. For example, the first counter magnetic film 11b and the second counter magnetic film 12b correspond to the second magnetic layer 20. For example, the first intermediate film 11c and the second intermediate film 12c correspond to the first intermediate layer 30.

As illustrated in FIG. 6B, for example, the first electrode 58a and the second electrode 58b are provided. For example, the first magnetic film 11a, the first counter magnetic film 11b, and the first intermediate film 11c are disposed between the first electrode 58a and the second electrode 58b.

As illustrated in FIG. 6D, for example, a third electrode 58c and a fourth electrode 58d are provided. For example, the second magnetic film 12a, the second counter magnetic film 12b, and the second intermediate film 12c are disposed between the third electrode 58c and the fourth electrode 58d.

In the example as illustrated in FIG. 6B, an insulating layer 58i is provided between the first electrode 58a and the structure body 70d. For example, the insulating layer 58i is provided also between the first electrode 58a and the second electrode 58b. For example, the insulating layer 58i is provided also between the third electrode 58c and the fourth electrode 58d. Electrical insulation between the electrodes is obtained by the insulating layer 58i.

As shown in FIG. 6C, the sensor 130 may further include a processor 68 (e.g., a processing circuit). The processor 68 is electrically connected to the first sensing elements 51 and the second sensing elements 52. For example, the processor 68 is electrically connected to the first electrode 58a, the second electrode 58b, the third electrode 58c, and the fourth electrode 58d. The processor 68 outputs a signal corresponding to the signal obtained from the first sensing elements 51. The processor 68 outputs a signal corresponding to the signal obtained from the second sensing elements 52. The processor 68 outputs a signal corresponding to the change of the electrical resistance occurring in the sensing elements.

In the example as shown in FIG. 6C, the deforming portion 70c (the outer edge 70r) is substantially a polygon (a quadrilateral, and specifically, a rectangle). The outer edge 70r of the deforming portion 70c includes a first side 70s1, a second side 70s2, a third side 70s3, and a fourth side 70s4.

Various configurations are applicable to the deforming portion 70c (the outer edge 70r). The deforming portion 70c (the outer edge 70r) may be, for example, substantially perfectly circular, flattened-circular (including elliptical), substantially square configuration, or rectangular. For example, in the case where the deforming portion 70c (the outer edge 70r) is substantially square or substantially rectangular, the portions at the four corners (the corner portions) may have curved configurations.

The first side 70s1 extends in the first direction (in the example, the X-axis direction). The second side 70s2 is separated from the first side 70s1 in a second direction. The second direction crosses the first direction. In the example, the second direction is the Y-axis direction. The second side 70s2 extends in the first direction (the X-axis direction). The third side 70s3 extends in the second direction (the Y-axis direction). The fourth side 70s4 is separated from the third side 70s3 in the first direction (the X-axis direction) and extends in the second direction (the Y-axis direction).

In the example, the distance along the first direction between the third side 70s3 and the fourth side 70s4 is longer than the distance along the second direction between the first side 70s1 and the second side 70s2. The deforming portion 70c is substantially a rectangle; and the first side 70s1 and the second side 70s2 are the long sides. The third side 70s3 and the fourth side 70s4 are the short sides.

When stress is applied to the deforming portion 70c, a large strain (an anisotropic strain) is generated at the vicinity of the outer edge 70r of the deforming portion 70c. By disposing the sensing elements at the vicinity of the outer edge 70r, a large strain is applied to the sensing elements; and high sensitivity is obtained.

In the example, the multiple first sensing elements 51 are arranged along the first side 70s1. The multiple second sensing elements 52 are arranged along the second side 70s2.

The SN ratio can be improved by connecting the multiple sensing elements in series. In the embodiment, the multiple sensing elements that obtain electrical signals of the same polarity when the pressure is applied can be disposed. Thereby, the SN ratio improves.

The embodiment may include an electronic device. The electronic device includes, for example, sensors according to the embodiments recited above and the sensors of modifications of the embodiments recited above. The electronic device includes, for example, an information terminal. The information terminal includes a recorder, etc. The electronic device includes a microphone, a blood pressure sensor, a touch panel, etc.

Figure 7:
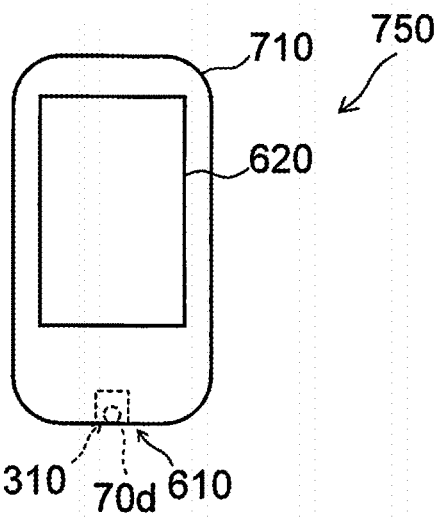
FIG. 7 is a schematic view illustrating an electronic device according to the embodiment.

FIG. 7 is a schematic view illustrating an electronic device according to the embodiment.

As shown in FIG. 7, the electronic device 750 according to the embodiment is, for example, an information terminal 710. For example, a microphone 610 is provided in the information terminal 710.

The microphone 610 includes, for example, a sensor 310. For example, the structure body 70d is substantially parallel to a surface where a displayer 620 of the information terminal 710 is provided. The arrangement of the structure body 70d is arbitrary. Any sensor described in reference to the embodiments recited above is applicable to the sensor 310.

Figure 8A:
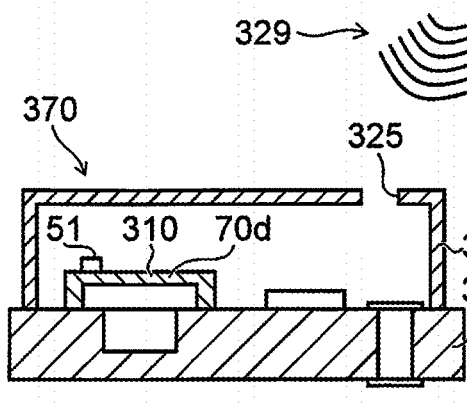
FIG. 8A and FIG. 8B are schematic cross-sectional views illustrating the electronic device according to the embodiment.
Figure 8B:
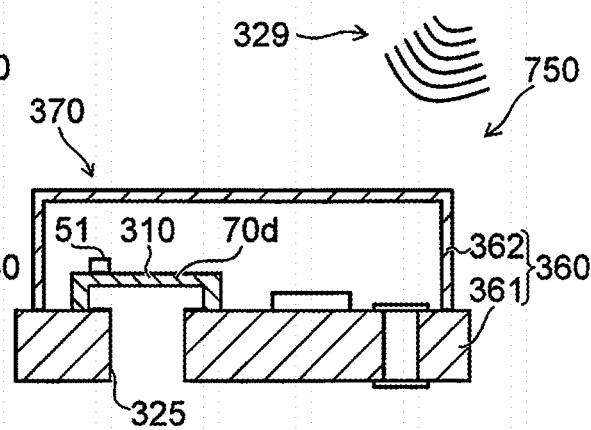

FIG. 8A and FIG. 8B are schematic cross-sectional views illustrating the electronic device according to the embodiment.

As shown in FIG. 8A and FIG. 8B, the electronic device 750 (e.g., a microphone 370 (an acoustic microphone)) includes a housing 360, a cover 362, and the sensor 310. The housing 360 includes, for example, a substrate 361 (e.g., a printed circuit board) and the cover 362. The substrate 361 includes, for example, a circuit such as an amplifier, etc.

An acoustic hole 325 is provided in the housing 360 (at least one of the substrate 361 or the cover 362). In the example shown in FIG. 8A, the acoustic hole 325 is provided in the cover 362. In the example shown in FIG. 8B, the acoustic hole 325 is provided in the substrate 361. Sound 329 passes through the acoustic hole 325 and enters the interior of the cover 362. The microphone 370 responds to the sound pressure.

For example, the sensor 310 is placed on the substrate 361; and an electrical signal line (not illustrated) is provided. The cover 362 is provided to cover the sensor 310. The housing 360 is provided around the sensor 310. At least a portion of the sensor 310 is provided inside the housing 360. For example, the first sensing element 51 and the structure body 70d are provided between the substrate 361 and the cover 362. For example, the sensor 310 is provided between the substrate 361 and the cover 362.

Figure 9A:
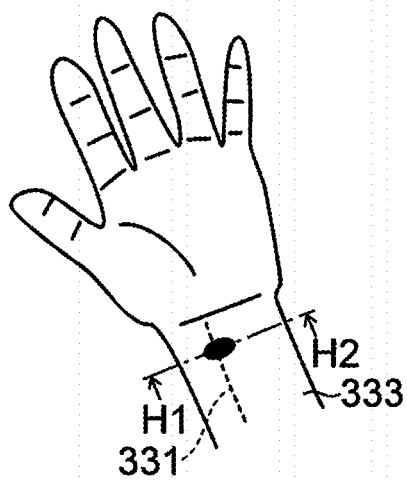
FIG. 9A and FIG. 9B are schematic views illustrating another electronic device according to the embodiment.
Figure 9B:
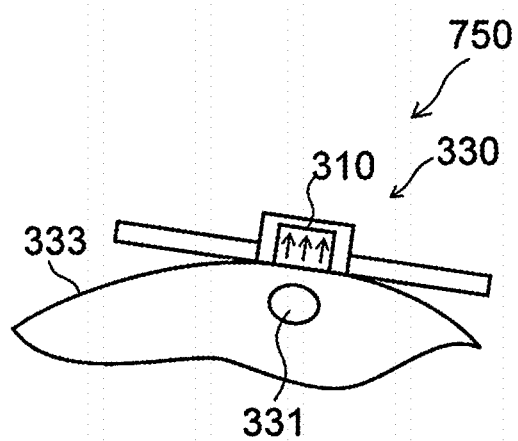

FIG. 9A and FIG. 9B are schematic views illustrating another electronic device according to the embodiment. In the example of these drawings, the electronic device 750 is a blood pressure sensor 330. FIG. 9A is a schematic plan view illustrating skin on an arterial vessel of a human. FIG. 9B is a line H1-H2 cross-sectional view of FIG. 9A.

The sensor 310 is used as the sensor in the blood pressure sensor 330. The sensor 310 contacts the skin 333 on the arterial vessel 331. Thereby, the blood pressure sensor 330 can continuously perform blood pressure measurements.

Figure 10:
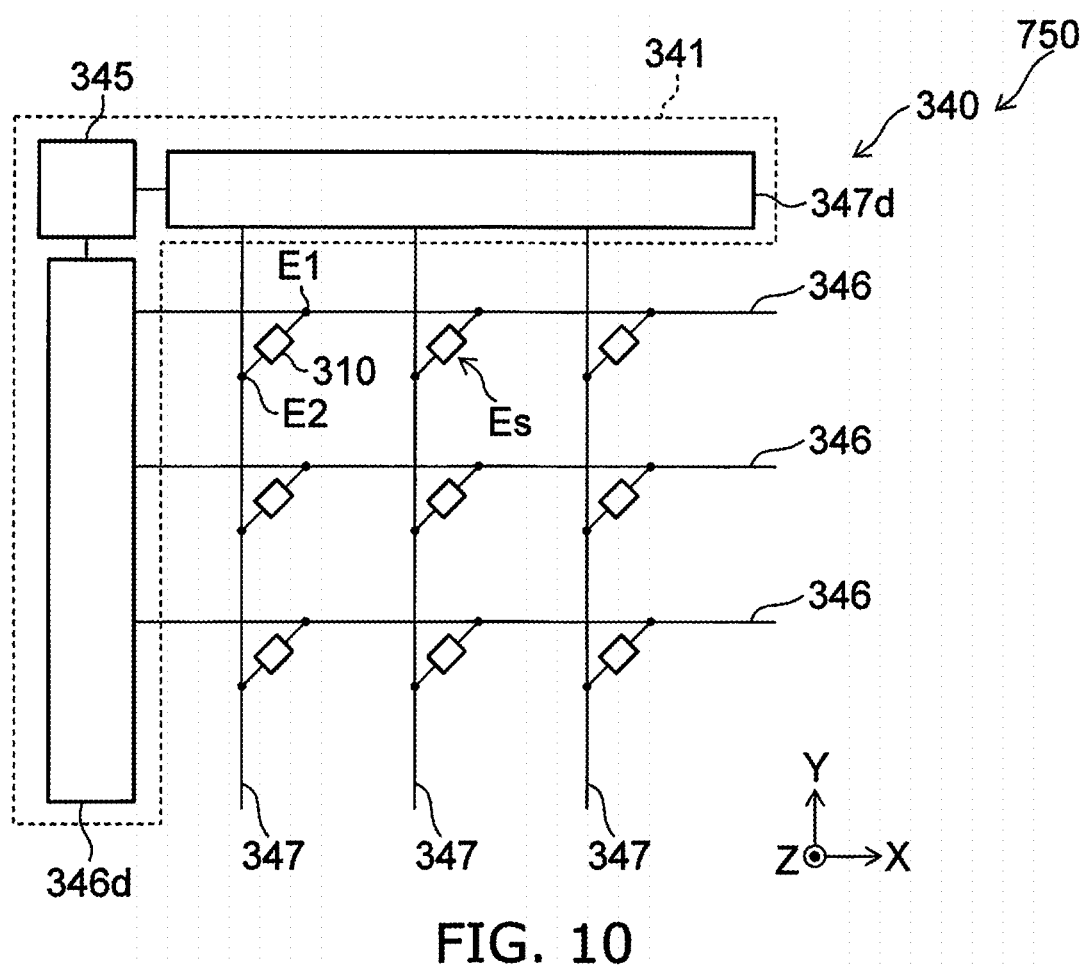
FIG. 10 is a schematic view illustrating another electronic device according to the embodiment.

FIG. 10 is a schematic view illustrating another electronic device according to the embodiment.

In the example of the drawing, the electronic device 750 is a touch panel 340. In the touch panel 340, the sensors 310 are provided in at least one of the interior of the display or the exterior of the display.

For example, the touch panel 340 includes multiple first interconnects 346, multiple second interconnects 347, the multiple sensors 310, and a control circuit 341.

In the example, the multiple first interconnects 346 are arranged along the Y-axis direction. Each of the multiple first interconnects 346 extends along the X-axis direction. The multiple second interconnects 347 are arranged along the X-axis direction. Each of the multiple second interconnects 347 extends along the Y-axis direction.

One of the multiple sensors 310 is provided at the crossing portion between the multiple first interconnects 346 and the multiple second interconnects 347. One of the sensors 310 is used as one of sensing components Es for detecting. The crossing portion includes the position where the first interconnect 346 and the second interconnect 347 cross and includes the region at the periphery of the position.

One end E1 of one of the multiple sensors 310 is connected to one of the multiple first interconnects 346. Another end E2 of the one of the multiple sensors 310 is connected to one of the multiple second interconnects 347.

The control circuit 341 is connected to the multiple first interconnects 346 and the multiple second interconnects 347. For example, the control circuit 341 includes a first interconnect circuit 346d connected to the multiple first interconnects 346, a second interconnect circuit 347d connected to the multiple second interconnects 347, and a control signal circuit 345 connected to the first interconnect circuit 346d and the second interconnect circuit 347d.

According to the embodiment, an electronic device that uses a sensor in which the sensitivity can be increased can be provided.

The embodiments include, for example, the following configurations (e.g., technological proposals).

Configuration 1

A sensor, comprising:

a structure body including a deforming portion, the deforming portion being deformable; and a first sensing element provided at the deforming portion, the first sensing element including first to fourth magnetic layers and a first intermediate layer, the first magnetic layer being provided between the second magnetic layer and the third magnetic layer, the fourth magnetic layer being provided between the first magnetic layer and the third magnetic layer, the first intermediate layer being provided between the second magnetic layer and the first magnetic layer, the third magnetic layer including at least one of a first material or a second material, the first material including at least one selected from the group consisting of Ir—Mn, Pt—Mn, Pd—Pt—Mn, and Ru—Rh—Mn, the second material including at least one of CoPt (a ratio of Co being not less than 50 at. % and not more than 85 at. %), $(Co_xPt_{100-x})_{100-y}Cr_y$ (x being not less than 50 at. % and not more than 85 at. %, and y being not less than 0 at. % and not more than 40 at. %), or FePt (a ratio of Pt being not less than 40 at. % and not more than 60 at. %), a crystallinity of at least a portion of the fourth magnetic layer being higher than a crystallinity of the first magnetic layer.

Configuration 2
    The sensor according to Configuration 1, wherein
    at least a portion of the first magnetic layer is amorphous, and
    the at least a portion of the fourth magnetic layer includes a crystal.

Configuration 3
    The sensor according to Configuration 1 or 2, wherein a thickness of the fourth magnetic layer is 1.4 nm or more.

Configuration 4
    The sensor according to any one of Configurations 1 to 3, wherein a ratio of a thickness of the fourth magnetic layer to a thickness of the first magnetic layer is not less than 0.175 and not more than 0.3.

Configuration 5
    The sensor according to Configuration 3, wherein a distance between the first magnetic layer and the fourth magnetic layer is 1 nm or less.

Configuration 6
    The sensor according to Configuration 5, wherein a thickness of the first magnetic layer is 5 nm or more.

Configuration 7
    The sensor according to any one of Configurations 1 to 6, wherein
    the first magnetic layer includes Fe and B, and
    the fourth magnetic layer includes at least one selected from the group consisting of Fe, Co, and Ni.

Configuration 8
    The sensor according to Configuration 7, wherein
    the first sensing element further includes an intermediate magnetic layer provided between the first magnetic layer and the first intermediate layer,
    the intermediate magnetic layer includes Fe, Co, and B, and
    a concentration of Co included in the first magnetic layer is lower than a concentration of Co included in the intermediate magnetic layer, or the first magnetic layer does not include Co.

Configuration 9
    The sensor according to any one of Configurations 1 to 8, wherein
    the first sensing element further includes a first nonmagnetic layer provided between the first magnetic layer and the fourth magnetic layer, and
    the first nonmagnetic layer includes at least one selected from the group consisting of Cu, Ru, Au, Ag, Cr, Ir, and Mg.

Configuration 10
    The sensor according to Configuration 9, wherein the first nonmagnetic layer contacts the first magnetic layer and the fourth magnetic layer.

Configuration 11
    The sensor according to any one of Configurations 1 to 10, wherein
    the first sensing element further includes a second nonmagnetic layer provided between the fourth magnetic layer and the third magnetic layer, and
    the second nonmagnetic layer includes at least one selected from the group consisting of Cu, Ru, Au, Ag, Cr, Ir, and Mg.

Configuration 12
    The sensor according to Configuration 11, wherein the second nonmagnetic layer contacts the fourth magnetic layer and the third magnetic layer.

Configuration 13
    The sensor according to any one of Configurations 1 to 12, wherein the first intermediate layer includes oxygen and at least one selected from the group consisting of Mg, Al, Ti, Zn, and Ga.

Configuration 14
    The sensor according to any one of Configurations 1 to 13, wherein an electrical resistance of the first sensing element changes according to a deformation of the deforming portion.

Configuration 15
    The sensor according to any one of Configurations 1 to 14, wherein a first magnetization of the first magnetic layer is tilted with respect to a second magnetization of the second magnetic layer.

Configuration 16
    The sensor according to any one of Configurations 1 to 14, wherein
    the structure body further includes a supporter,
    the deforming portion includes a connection portion connected to the supporter,
    the connection portion is aligned with a first connection direction, and
    a first magnetization of the first magnetic layer is tilted with respect to the first connection direction.

Configuration 17
    The sensor according to any one of Configurations 1 to 16, wherein an absolute value of an angle between the first magnetization and the first connection direction is not less than 10 degrees and not more than 80 degrees.

Configuration 18
    A microphone, comprising the sensor according to any one of Configurations 1 to 17.

Configuration 19
    A blood pressure sensor, comprising the sensor according to any one of Configurations 1 to 17.

Configuration 20
    A touch panel, comprising the sensor according to any one of Configurations 1 to 17.

According to the embodiments, a sensor, a microphone, a blood pressure sensor, and a touch panel are provided in which the sensitivity can be increased.

In the specification of the application, "perpendicular" and "parallel" refer to not only strictly perpendicular and strictly parallel but also include, for example, the fluctuation due to manufacturing processes, etc. It is sufficient to be substantially perpendicular and substantially parallel.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in sensors such as structure bodies, sensing elements, magnetic layers, intermediate layers, electrodes, processors, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all sensors, microphones, blood pressure sensors, and touch panels practicable by an appropriate design modification by one skilled in the art based on the sensors, the microphones, the blood pressure sensors, and the touch panels described above as embodiments of the invention also are within the scope of the invention to the extent that the purport of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A sensor, comprising:
a structure body including a deforming portion, the deforming portion being deformable; and
a first sensing element provided at the deforming portion, the first sensing element including first to fourth magnetic layers and a first intermediate layer,
the first magnetic layer being provided between the second magnetic layer and the third magnetic layer,
the fourth magnetic layer being provided between the first magnetic layer and the third magnetic layer,
the first intermediate layer being provided between the second magnetic layer and the first magnetic layer,
the third magnetic layer including at least one of a first material or a second material, the first material including at least one selected from the group consisting of Ir—Mn, Pt—Mn, Pd—Pt—Mn, and Ru—Rh—Mn, the second material including at least one of CoPt (a ratio of Co being not less than 50 at. % and not more than 85 at. %), $(Co_xPt_{100-x})_{100-y}Cr_y$ (x being not less than 50 at. % and not more than 85 at. %, and y being not less than 0 at. % and not more than 40 at. %), or FePt (a ratio of Pt being not less than 40 at. % and not more than 60 at. %),
a crystallinity of at least a portion of the fourth magnetic layer being higher than a crystallinity of the first magnetic layer.

2. The sensor according to claim 1, wherein
at least a portion of the first magnetic layer is amorphous, and
the at least a portion of the fourth magnetic layer includes a crystal.

3. The sensor according to claim 1, wherein a thickness of the fourth magnetic layer is 1.4 nm or more.

4. The sensor according to claim 3, wherein a distance between the first magnetic layer and the fourth magnetic layer is 1 nm or less.

5. The sensor according to claim 4, wherein a thickness of the first magnetic layer is 5 nm or more.

6. The sensor according to claim 1, wherein a ratio of a thickness of the fourth magnetic layer to a thickness of the first magnetic layer is not less than 0.175 and not more than 0.3.

7. The sensor according to claim 1, wherein
the first magnetic layer includes Fe and B, and
the fourth magnetic layer includes at least one selected from the group consisting of Fe, Co, and Ni.

8. The sensor according to claim 7, wherein
the first sensing element further includes an intermediate magnetic layer provided between the first magnetic layer and the first intermediate layer,
the intermediate magnetic layer includes Fe, Co, and B, and
a concentration of Co included in the first magnetic layer is lower than a concentration of Co included in the intermediate magnetic layer, or the first magnetic layer does not include Co.

9. The sensor according to claim 1, wherein
the first sensing element further includes a first nonmagnetic layer provided between the first magnetic layer and the fourth magnetic layer, and
the first nonmagnetic layer includes at least one selected from the group consisting of Cu, Ru, Au, Ag, Cr, Ir, and Mg.

10. The sensor according to claim 9, wherein the first nonmagnetic layer contacts the first magnetic layer and the fourth magnetic layer.

11. The sensor according to claim 1, wherein
the first sensing element further includes a second nonmagnetic layer provided between the fourth magnetic layer and the third magnetic layer, and
the second nonmagnetic layer includes at least one selected from the group consisting of Cu, Ru, Au, Ag, Cr, Ir, and Mg.

12. The sensor according to claim 11, wherein the second nonmagnetic layer contacts the fourth magnetic layer and the third magnetic layer.

13. The sensor according to claim 1, wherein the first intermediate layer includes oxygen and at least one selected from the group consisting of Mg, Al, Ti, Zn, and Ga.

14. The sensor according to claim 1, wherein an electrical resistance of the first sensing element changes according to a deformation of the deforming portion.

15. The sensor according to claim 1, wherein a first magnetization of the first magnetic layer is tilted with respect to a second magnetization of the second magnetic layer.

16. The sensor according to claim 1, wherein
the structure body further includes a supporter,
the deforming portion includes a connection portion connected to the supporter,
the connection portion is aligned with a first connection direction, and
a first magnetization of the first magnetic layer is tilted with respect to the first connection direction.

17. The sensor according to claim 1, wherein an absolute value of an angle between the first magnetization and the first connection direction is not less than 10 degrees and not more than 80 degrees.

18. A microphone, comprising the sensor according to claim 1, wherein the deforming portion is deformable by sound.

19. A blood pressure sensor, comprising the sensor according to claim 1, wherein the deforming portion is deformable by blood pressure.

20. A touch panel, comprising the sensor according to claim 1, wherein the deforming portion is deformable by touch.

* * * * *